(12) United States Patent
Berman

(10) Patent No.: US 9,301,779 B2
(45) Date of Patent: Apr. 5, 2016

(54) DEVICE FOR ARTIFICIAL INSEMINATION

(71) Applicant: Stephanie Berman, Boston, MA (US)

(72) Inventor: Stephanie Berman, Boston, MA (US)

(*) Notice: Subject to any disclaimer, the term of this patent is extended or adjusted under 35 U.S.C. 154(b) by 91 days.

(21) Appl. No.: 14/109,130

(22) Filed: Dec. 17, 2013

(65) Prior Publication Data

US 2014/0200400 A1 Jul. 17, 2014

Related U.S. Application Data

(60) Provisional application No. 61/738,576, filed on Dec. 18, 2012.

(51) Int. Cl.
*A61F 5/00* (2006.01)
*A61B 17/43* (2006.01)
*A61H 19/00* (2006.01)

(52) U.S. Cl.
CPC ............... *A61B 17/43* (2013.01); *A61H 19/44* (2013.01); *A61H 19/50* (2013.01); *A61H 2201/0153* (2013.01); *A61H 2201/1688* (2013.01)

(58) Field of Classification Search
CPC ..... A61H 19/00; A61H 19/02; A61H 19/027; A61H 19/44; A61H 2201/105; A61H 2201/1253; A61B 17/425; A61B 17/43
USPC .......................................... 600/38–41, 33–35
See application file for complete search history.

(56) References Cited

U.S. PATENT DOCUMENTS

| 2009/0030268 A1* | 1/2009 | Stroud | 600/35 |
| 2011/0224482 A1* | 9/2011 | McCarthy et al. | 600/35 |
| 2013/0324792 A1* | 12/2013 | Mizrahi et al. | 600/38 |
| 2014/0107410 A1* | 4/2014 | Rosenberg | 600/38 |

* cited by examiner

*Primary Examiner* — John Lacyk
(74) *Attorney, Agent, or Firm* — Bay State IP, LLC

(57) ABSTRACT

A device for artificial insemination, wherein the device includes a dildo member having an internal channel for receiving a tubing connected to a pumping mechanism and associated pumping arm, wherein fluid may be drawn into the dildo member through the pumping mechanism and discharged through the internal tubing at a distal end.

6 Claims, 6 Drawing Sheets

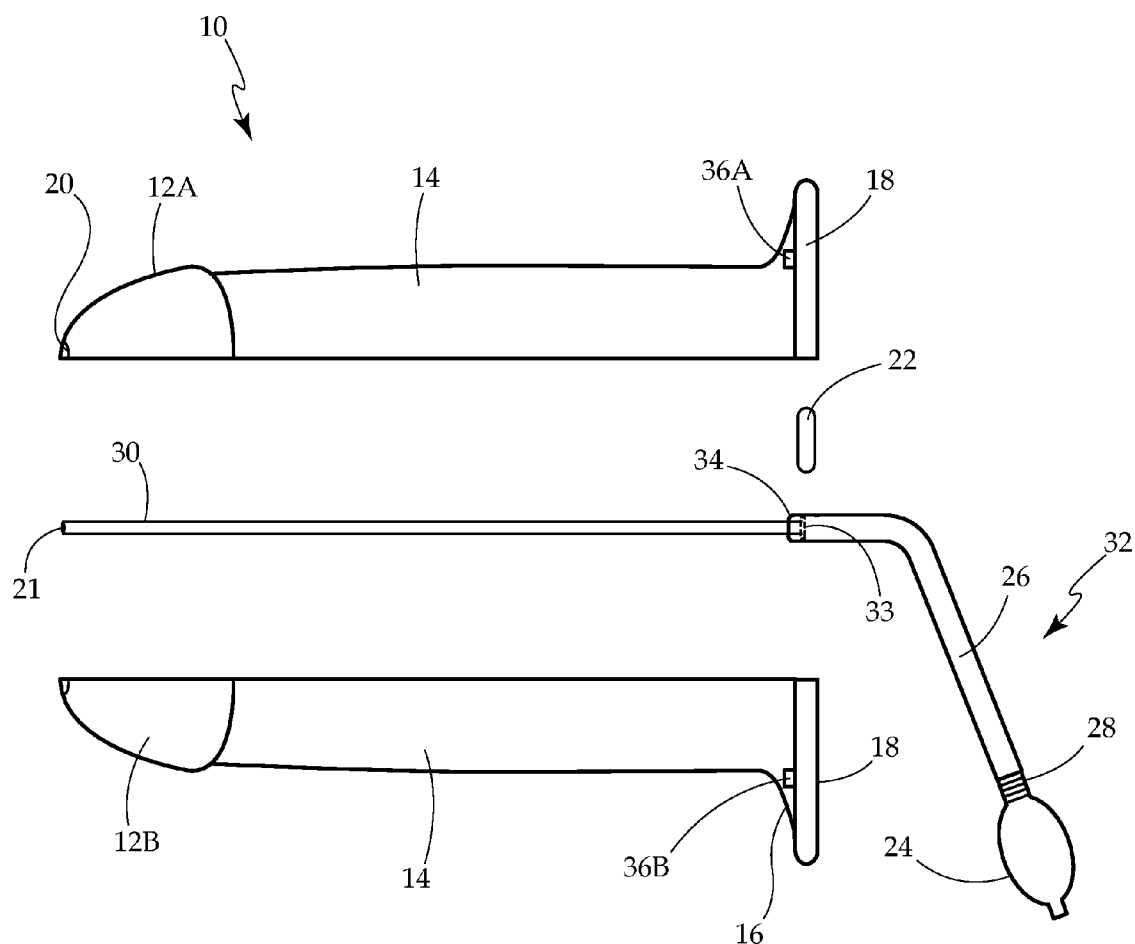
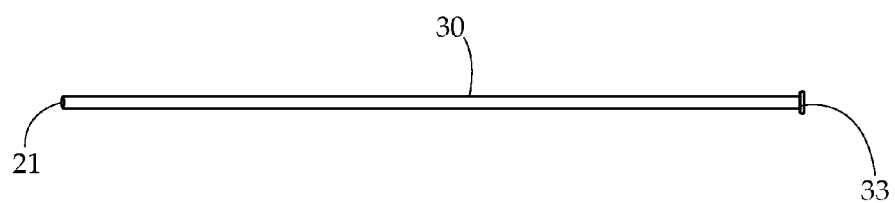
Fig. 3
Fig. 4

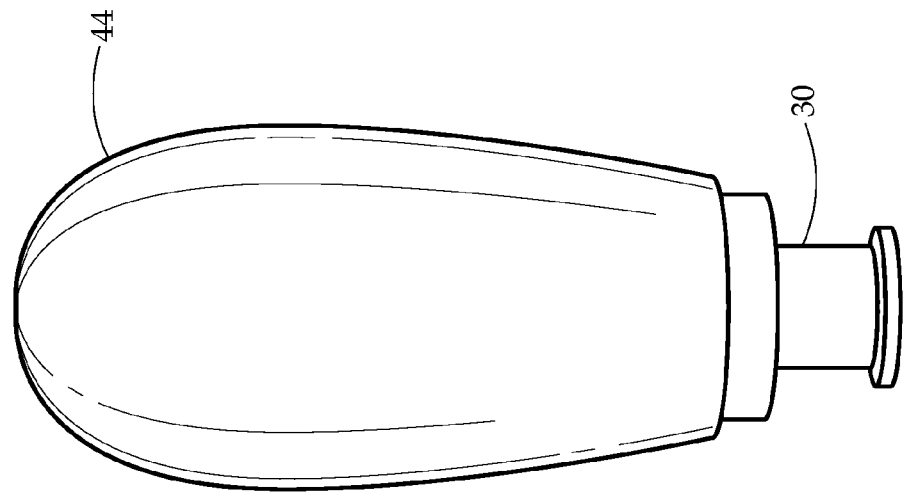
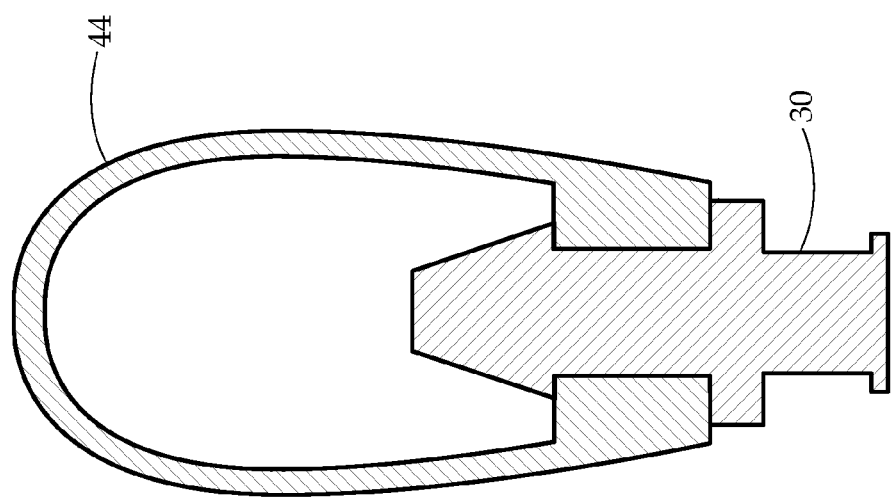

DEVICE FOR ARTIFICIAL INSEMINATION

CROSS REFERENCE TO RELATED APPLICATION

This application claims the benefit of and takes priority from U.S. Provisional Patent Application Ser. No. 61/738,576, filed on Dec. 18, 2012, the contents of which are herein incorporated by reference.

BACKGROUND OF THE INVENTION

Field of the Invention

The invention generally relates to devices for artificial insemination, and more particularly, to devices that mimic ejaculation.

Many couples, upon wishing to conceive, undertake the act of copulation with the goal of insemination. However, for a variety of reasons, couples may not be able to achieve conception via traditional means. For example, same-sex or transgender couples may not possess the necessary biological equipment, or perhaps a single woman would like to conceive without relying on a partner. Similarly, heterosexual couples may not be able to conceive where the male is unable to produce sperm, whether caused by erectile dysfunction, a low sperm count, or related issues stemming from testicular cancer. In these cases, couples may turn to artificial means for insemination.

Typically, artificial insemination is accomplished with a syringe. Sperm is drawn into the syringe and then injected into a woman's vagina, allowing anyone with access to a sperm sample the opportunity to conceive. While syringes accomplish the goal of conception, their usage lacks the intimate and relational properties of sexual intercourse.

Couples may also inseminate by using a device that both mimics sexual intercourse and also delivers a sperm sample at the appropriate time. For example, couples may employ a sexual device resembling an erect penis in shape, size, and overall appearance (commonly referred to as a dildo) to have pseudo genital-to-genital sexual intercourse. When the dildo is coupled with cylindrical tubing running through the inside and attached at the end to a silicone bulb, it allows a specimen to be drawn into the tubing and expelled. Couples are able to manually inseminate while also having an intimate sexual experience.

Due to the fact that dildos are inserted into the vagina, cleaning after use is very important to prevent infection and other health issues. To ensure sanitization, cleaning must be meticulous and thorough. The dildo may be cleaned by hand with soap and water, which may not fully clean the inside of the rubber tubing. The rubber tubing can be further cleaned by running a cleaning solution and water through the tube, which may not be adequate. Running the dildo through a mechanical device for cleaning utensils, such as a dishwasher, may melt the internal tubing or the dildo itself. All of these issues may result in infrequent and insufficient cleanings, leading to possible health implications. Further, despite cleaning, it can never be guaranteed that the object is completely sanitized.

SUMMARY OF THE INVENTION

The instant apparatus and system, as illustrated herein, is clearly not anticipated, rendered obvious, or even present in any of the prior art mechanisms, either alone or in any combination thereof. Thus the several embodiments of the instant apparatus are illustrated herein.

In accordance with the invention, the problem of completely and quickly sanitizing a dildo that simulates ejaculation is solved by a dildo that incorporates interchangeable internal tubing. In this way, the tubing is simply thrown away after a single use and replaced with a new one. As the new tubing has never been used, it can be guaranteed that it is completely sanitized. Extensive, yet insufficient efforts for cleaning are no longer required.

Therefore, it is an object of the present invention to provide a dildo that provides for artificial insemination that allows for easy cleaning.

It is another object of the present invention to provide a dildo that includes a silicone "tree" built inside the dildo to allow for the silicone tubing to glide through the entire length of the dildo with no difficulty. It is quite difficult to successfully slide silicone materials on or in silicone materials. This tree allows the ease of that transfer of the tubing internally through the dildo.

It is another object of the present invention to provide a dildo that has a custom tip designed to lock the inner tubing in place when used to mimic intercourse. This custom tip allows for the successful transfer and delivery of the liquid and also enables the tubing to be locked into place or removed.

It is another object of the present invention to provide a dildo that includes a chamber at the base of the apparatus which allows for the inner tubing to be placed inside the chamber and lay flat. This allows the user to wear the apparatus and not have the inner tubing sticking out anywhere.

It is another object of the present invention to provide a means for couples to artificially inseminate.

It is a further object of the present invention to provide a dildo that mimics ejaculation.

It is yet another object of the present invention to provide a means for artificial insemination that is sanitary despite repeated use.

The invention features a dildo with a removable inner lining. The removable inner lining may be a silicone tube. The removable inner lining may be attached to a pump, and the pump may be a rubber bulb.

There has thus been outlined, rather broadly, the more important features of the device for artificial insemination in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

These together with other objects of the invention, along with various features of novelty, which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

To the accomplishment of the foregoing and related ends, certain illustrative aspects are described herein and these aspects are indicative of the various ways in which the principles disclosed herein can be practiced and all aspects and equivalents thereof are intended to be within the scope of the claimed subject matter.

BRIEF DESCRIPTION OF THE DRAWINGS

Advantages of the present apparatus will be apparent from the following detailed description of exemplary embodiments thereof, which description should be considered in conjunction with the accompanying drawings, in which: Having thus described the invention in general terms, reference will now be made to the accompanying drawings, which are not necessarily drawn to scale, and wherein:

FIG. 3 is an exploded view of one embodiment of the instant invention, illustrating the dildo separated into two halves, with the tubing associated with one halve.

FIG. 4 is a side elevation view of one embodiment of the internal tubing utilized in conjunction with the dildo.

FIGS. 9A and 9B is a cross-sectional view of a custom tip that is designed to lock the inner tubing in place during use.

DETAILED DESCRIPTION OF THE EMBODIMENTS

The detailed description set forth below in connection with the appended drawings is intended as a description of presently preferred embodiments of the invention and does not represent the only forms in which the present invention may be constructed and/or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention, such as artificial insemination devices with removable inner linings of different sizes, dimensions, and construction materials.

Figure 1:
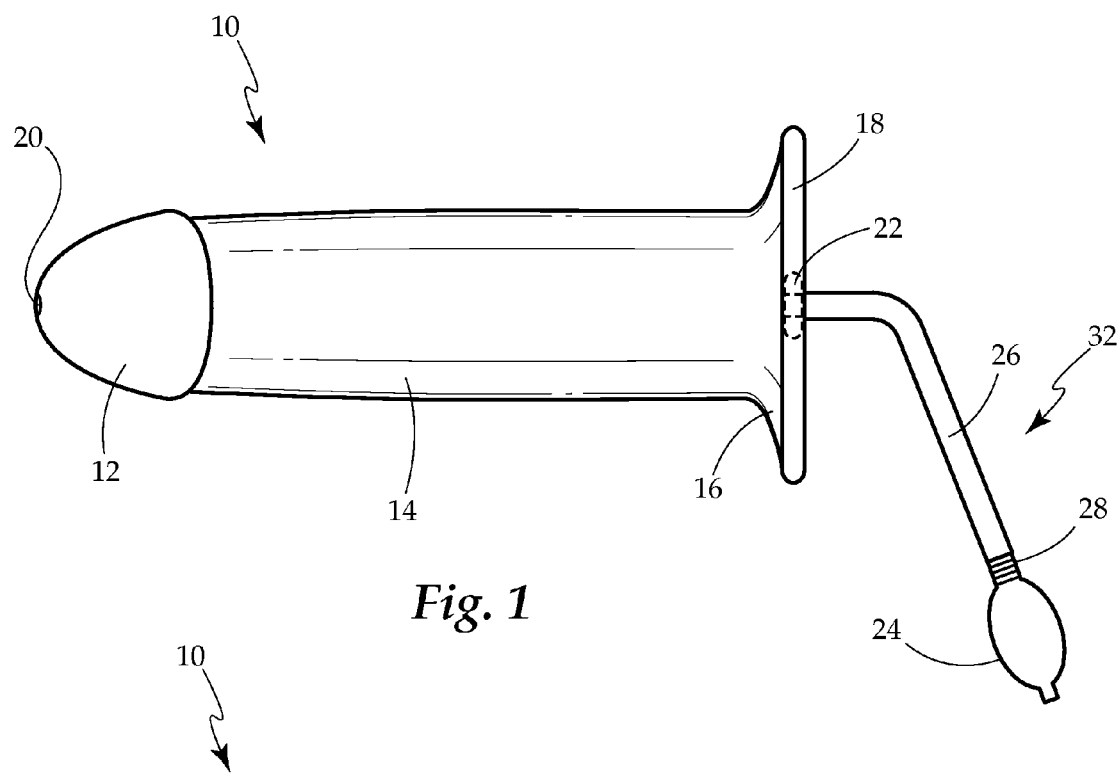
FIG. 1 is a side view of one embodiment of the instant invention displaying a dildo and associated tubing.
Figure 2:
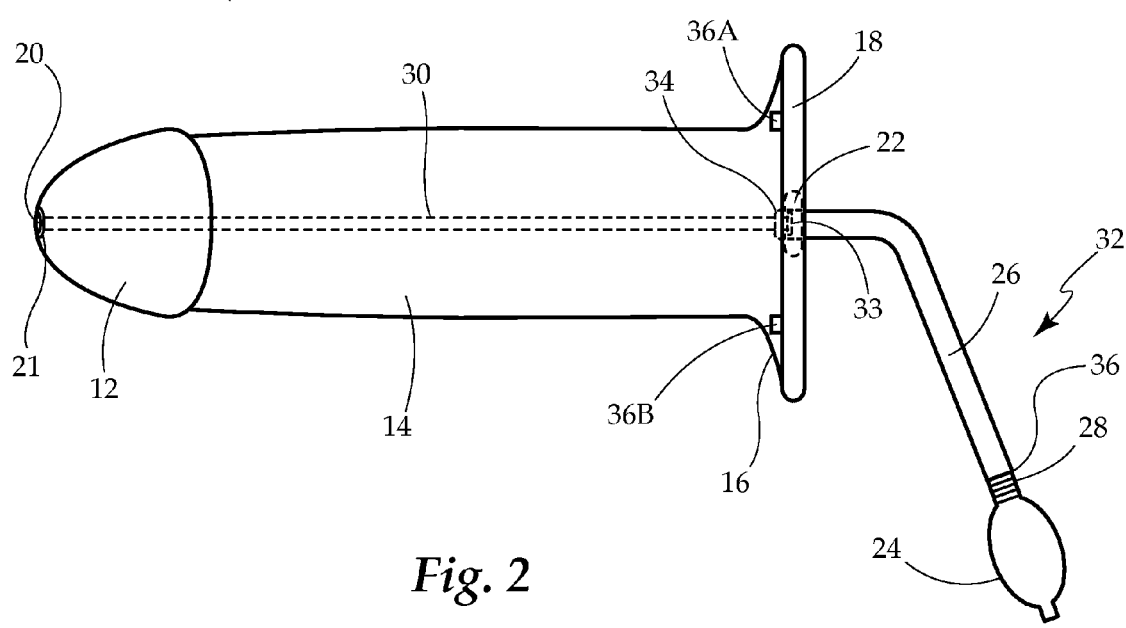
FIG. 2 is a cross-sectional view of one embodiment of the instant invention, wherein the tubing is shown extending internally through the dildo.
Figure 5:
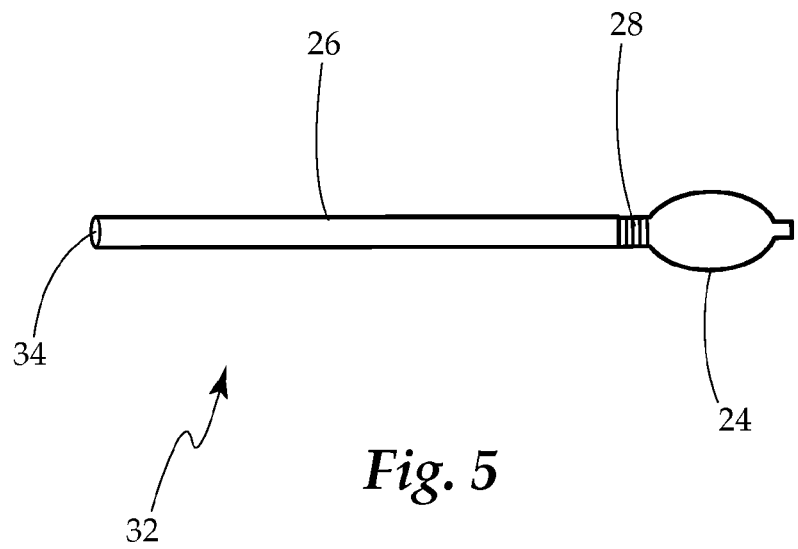
FIG. 5 is a side elevation view of a pumping mechanism in communication with a pumping arm that connects to the internal tubing.
Figure 6:
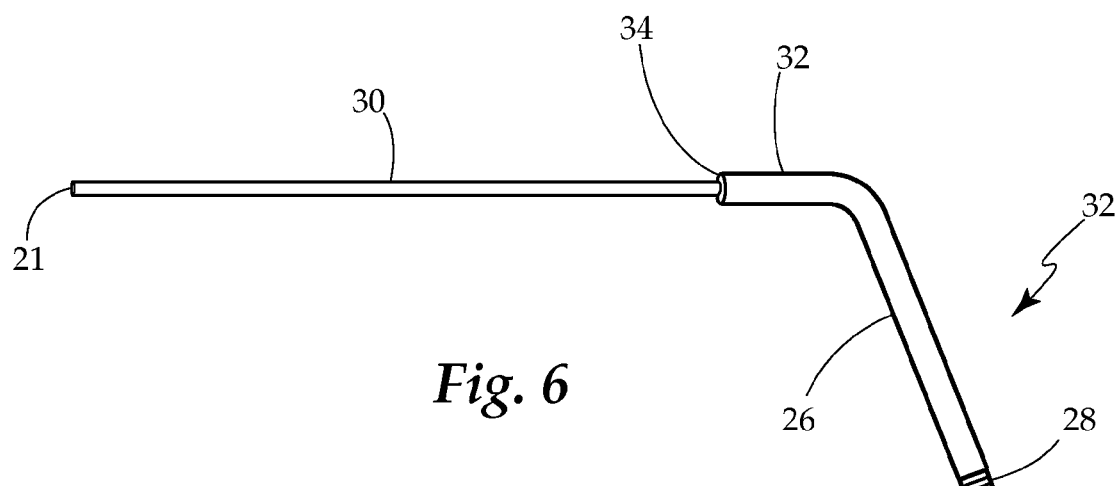
FIG. 6 is a side elevation view of a pumping mechanism and associated pumping arm connected to the internal tubing located within the dildo.

Referring to FIG. 1, an embodiment of the present invention is presented. A dildo 10, made preferably of a medical grade silicone material is shown, which comprises a distal end (head) 12, a shaft 14, and a proximal end 16. The proximal end increases longitudinally in diameter to meet a base 18. The overall appearance of the dildo 10 is such that it resembles an erect penis. Within the dildo 10 runs a thin silicone tube, which is visible and exposed at the distal end 12 as an end port 21 (see FIG. 3) extending from an opening 20 at the distal end 12.

In one embodiment, the base 18 is removable so as to allow for the plastic tubing embedded in the middle of the dildo 10 to be replaced per use. The base 18 is preferably made from a medical grade silicone material, and features an opening 22, from which a proximal end 33 of the internal tubing extends. A pumping mechanism 32, comprising a rubber bulb 24 affixed to a pumping arm 26, is then affixed to the proximal end 33. Fluid may then be drawn into the dildo by pressing the rubber bulb.

In yet another embodiment, the base 18 does not need to be removeable in order to replace the inner tubing; a user may remove the inner tubing from the pump tubing, and then replace both sets of tubing prior to reassembly. In essence, a user may remove the tubing first, replace the catheter inside the dildo 10, and then re-attach the tubing with the pump for re-use.

In use, the dildo can be put into a harness of any kind and worn by a woman to simulate intercourse. The embedded silicone tubing and silicone tubing with rubber bulb pump are used in conjunction with the dildo to mimic intercourse and ejaculation. The device provides a woman or two women with the ability to achieve sexual pleasure and mimic ejaculation. This can also be used with other liquid materials other than semen to simulate ejaculation. The device can be used as a novelty item for fetish users who want to "ejaculate" other liquids out of the dildo.

Referring to FIGS. 2 through 6, each element of an embodiment of the present invention is presented in detail. Within the dildo 10, internal tubing 30 runs longitudinally across the shaft 14. The section of tubing at the opening 20 extends past the distal end by a small distance. At the proximal end, the internal tubing 30 attaches to a hub 22. The hub is slightly larger than the tubing and provides a point to attach a pumping mechanism 32.

In this embodiment of the present invention, the pumping mechanism 32 comprises a bulb 24, which is attached to the distal end 36 of a pumping arm 26 with an insert piece 28. The proximal end 34 of the short piece of tubing is placed through the opening 22 in the base 18, and fits snugly over the hub 33, thus creating a single waterproof channel from the bulb 24 to the opening 20 of the dildo 10.

Figure 7:
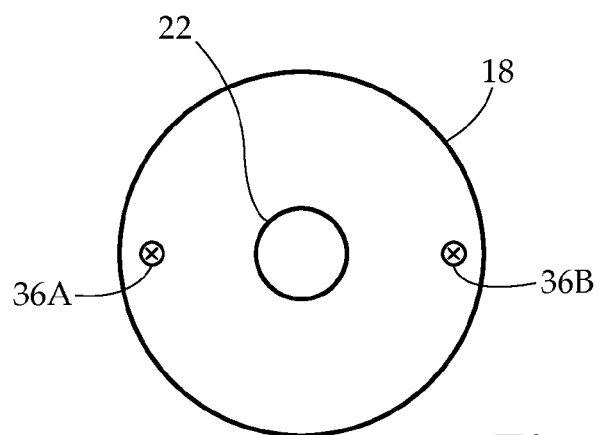
FIG. 7 is a cross-sectional front view of an embodiment of the pumping arm and base of the dildo.

Referring to FIG. 7, the base 18 of an embodiment of the present invention is presented in detail. The base 18 may be attached to the proximal end of the dildo 10 using two screws or bolts 36A 36B. The base may also be attached using hinges. The base is removable, allowing for the plastic tubing embedded in the middle of the dildo to be replaced per use. The base features an opening 22, wherein the internal tubing 30 ends and is affixed to the pumping mechanism 32.

Figure 8B:
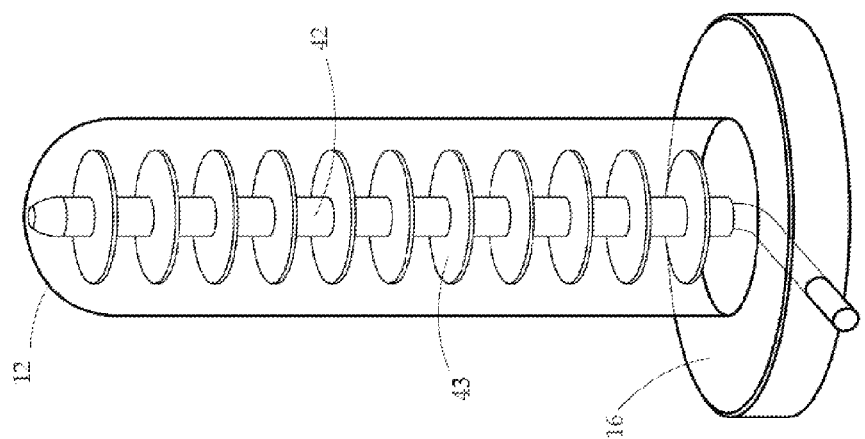
FIGS. 8A and 8B is side view of an alternate embodiment of the instant invention displaying a dildo and a guiding mechanism that encompasses the associated tubing.
Figure 8A:
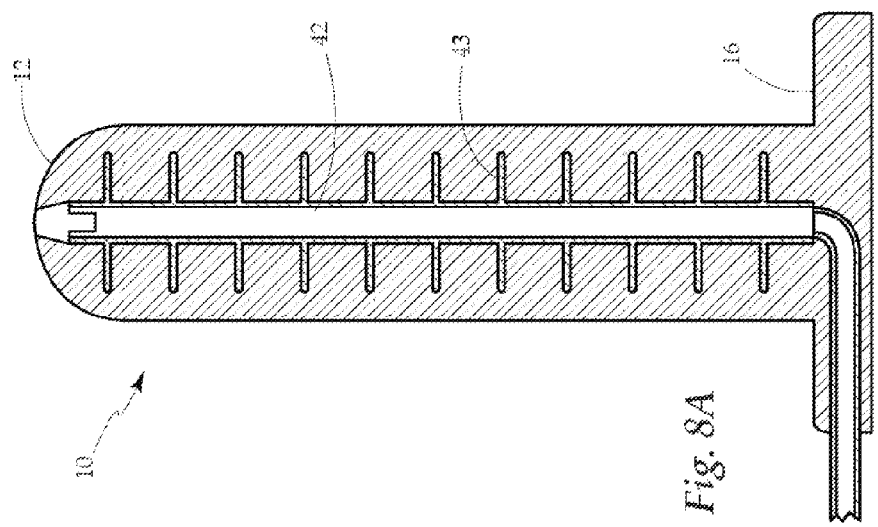

FIGS. 8A and 8B illustrates an alternative embodiment of the instant invention, wherein the dildo 10, further comprises a guiding mechanism 42, wherein the guiding mechanism 42 extends from the proximal end 12 to the distal end 16 of the dildo 10. Furthermore, the guiding mechanism 42 includes a plurality of circular elements 43 extending outwardly from the guiding mechanism 42 and equidistantly disposed along the guiding mechanism 42. Additionally, the internal tubing 30 is contained within the guiding mechanism 42 to allow for the internal tubing 30 to glide through the entire length of the dildo with no difficulty. It is quite difficult to successfully slide silicone materials on or in silicone materials and the guiding mechanism 42 allows for the ease of that transfer of the internal tubing 30 internally through the dildo 10.

FIGS. 9A and 9B illustrates an alternate embodiment of the instant invention, wherein a custom tip 44 is provided to lock the internal tubing 30 in place when used to mimic intercourse. This custom tip 44 allows for the successful transfer and delivery of the liquid and also enables the internal tubing 30 to be locked into place or removed. When this custom tip 44 is in place, it will lock the internal tubing 30 in and prevent it from moving while inside the shaft of the penis. If the tip is removed, the tubing will glide freely throughout the distance of the penis.

Figure 10A:
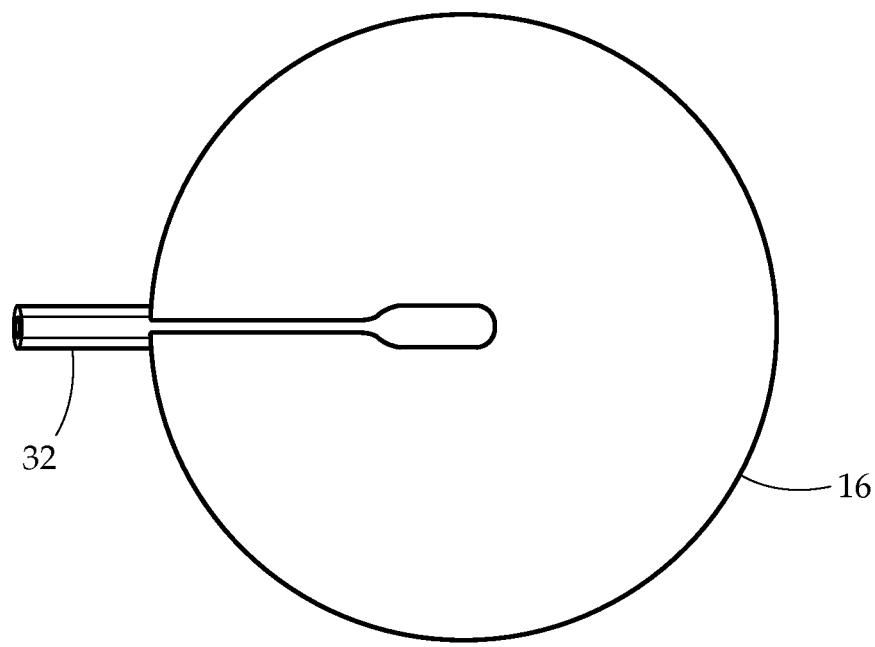
FIG. 10A is a bottom view of an alternative base which includes a chamber to allow the inner tubing to be placed inside the chamber.
Figure 10B:
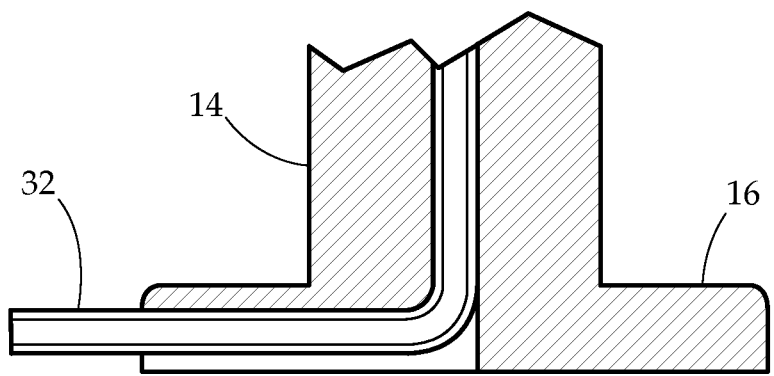
FIG. 10B is a cross-section view of the alternative base with the chamber.

FIGS. 10A and 10B illustrates an alternative embodiment of the base 18, wherein the base 18 further includes a chamber 46 within the base 18 which allows for the inner tubing to be placed inside the chamber and lay flat. This allows the user to wear the apparatus and not have the inner tubing sticking out anywhere.

It should be noted that we do not intend the invention to be limited by the present embodiments. For example, the pumping mechanism could include a variety of mechanisms. In another embodiment, the dildo could contain a lever for drawing the liquid into the plastic tubing embedded within the middle of the dildo. A lever or button mechanism could then trigger the release of the liquid in order to mimic ejaculation. Similarly, the tubing used throughout may be composed of rubber, plastic, or any combination of flexible and waterproof material.

In conclusion, herein is presented a device for artificial insemination that is easily cleaned by way of a removable lining. The invention is illustrated by example in the drawing figures, and throughout the written description. It should be understood that numerous variations are possible, while adhering to the inventive concept. Such variations are contemplated as being a part of the present invention.

What is claimed is:

1. An apparatus for sexual pleasure and artificial insemination comprising:
   a dildo member, wherein the dildo member comprises a proximal end and a distal end;
   a guiding mechanism, wherein the guiding mechanism extends from the proximal end to the distal end and further comprises a plurality of circular elements extending outwardly from and equidistantly disposed along the guiding mechanism;
   a cylindrical tubing, wherein the cylindrical tubing is contained within the guiding mechanism; and
   a pumping mechanism attached to the cylindrical tubing at the proximal end of the dildo member through a pumping arm.

2. The apparatus for sexual pleasure and artificial insemination of claim 1, further comprising:
   a base member attached to the proximal end of the dildo member; and
   an opening within the base member, wherein the pumping mechanism is removably attached to the cylindrical tubing through said opening.

3. The apparatus for sexual pleasure and artificial insemination of claim 2, wherein the base further comprises a chamber located within the base to enable the inner tubing to lay flat against the base.

4. The apparatus for sexual pleasure and artificial insemination of claim 1, wherein the dildo member is a material selected from the group consisting of silicone.

5. The apparatus for sexual pleasure and artificial insemination of claim 1, wherein the base member is removably attached to the proximal end of the dildo member.

6. The apparatus for sexual pleasure and artificial insemination of claim 1, wherein the base member is removably attached to the proximal end of the dildo member with at least one bolt.

* * * * *